United States Patent
Audeon

(10) Patent No.: US 9,488,587 B2
(45) Date of Patent: Nov. 8, 2016

(54) SYSTEM FOR DETECTING DOUBLE-FEED FLAT ITEMS

(71) Applicant: NEOPOST TECHNOLOGIES, Bagneux (FR)

(72) Inventor: David Audeon, Massy (FR)

(73) Assignee: NEOPOST TECHNOLOGIES, Bagneux (FR)

(*) Notice: Subject to any disclaimer, the term of this patent is extended or adjusted under 35 U.S.C. 154(b) by 113 days.

(21) Appl. No.: 14/606,620

(22) Filed: Jan. 27, 2015

(65) Prior Publication Data
US 2015/0219566 A1 Aug. 6, 2015

(30) Foreign Application Priority Data
Jan. 31, 2014 (EP) .................... 14290021

(51) Int. Cl.
*G01N 21/86* (2006.01)
*B65H 7/12* (2006.01)
*B65H 43/04* (2006.01)
*B65H 43/08* (2006.01)

(52) U.S. Cl.
CPC ............. *G01N 21/86* (2013.01); *B65H 7/125* (2013.01); *B65H 43/04* (2013.01); *B65H 43/08* (2013.01); *B65H 2511/13* (2013.01); *B65H 2511/30* (2013.01); *B65H 2553/414* (2013.01); *B65H 2557/51* (2013.01); *B65H 2701/1916* (2013.01); *G01N 2201/02* (2013.01); *G01N 2201/06113* (2013.01)

(58) Field of Classification Search
CPC ..................................................... B65H 7/125
USPC ......................................... 250/559.38, 559.4
See application file for complete search history.

(56) References Cited

U.S. PATENT DOCUMENTS

| 5,222,729 A | 6/1993 | Wallaschkowski |
| 6,761,352 B2 | 7/2004 | Scicluna et al. |
| 2004/0094012 A1 | 5/2004 | Liu |
| 2006/0210286 A1* | 9/2006 | Lee .................... G03G 15/6561 399/16 |

FOREIGN PATENT DOCUMENTS

WO 03/024849 A1 3/2003

OTHER PUBLICATIONS

European Search Report of EP 14 29 0021 dated Jun. 30, 2014.

* cited by examiner

*Primary Examiner* — Thanh Luu
(74) *Attorney, Agent, or Firm* — Seed IP Law Group LLP

(57) ABSTRACT

A system for detecting double-feed flat item conveyed in a mail processing machine, including a detection for directing a beam of radiant energy toward the moving flat items, scanning them with the beam and receiving at least a portion of the beam of radiation reflected from them. The detector includes a triangulation sensor for providing an output proportional to the position at which the reflected portion of the beam is received, and means for determining from the output, the distance (d) between the radiation source and the point of reflection of the beam on the moving flat items, and providing a signal (S) representative of said distance; and a controller configured to receive the signal (S) and generate an output signal (V) indicative of a flat item profile and a double-feed condition when it detects a significant break point or slope change of the signal from a first direction to a second direction.

13 Claims, 4 Drawing Sheets

SYSTEM FOR DETECTING DOUBLE-FEED FLAT ITEMS

TECHNICAL FIELD

The present invention relates to mail processing machines and more particularly to a system for efficiently detecting on the fly double-feed flat items such as documents or mail articles conveyed at high rates of speed in a franking, sorting or inserting machine.

PRIOR ART

Flat item processing systems typically comprise in particular de-stackers or singulators for withdrawing the flat items one at a time from a stack of superimposed flat items before feeding them to a conveyor path along which they travel separately.

A common problem with singulator mechanisms is that they occasionally extract and feed two or more items into the transport path, known as a "double feeds". Double-feeds are due e.g. to friction, electrostatic or glue adhesion, high mechanical pressure, and poor set-up or perfectible reliability of the singulator mechanism. They can evidently cause a range of various problems such as item jam, item damage, excessive wear, mishandling, machine down-time, time-consuming repair, additional cost and a reduced quality of service, in particular when their detection occurs at a late stage in the processing cycle.

On a typical franking machine, double-feed rates of around 0.5% of the mail flow can be anticipated (i.e 100 double-feed for a cadence of 20000 envelopes per hour) whereas they can easily reach or even exceed twice as much on a typical sorting machine.

Prior art comprises e.g. the following patent references.

EP 1 796 992 relates to a method of detecting double-feed of mail items that allows difficult mail types to be processed correctly, wherein simultaneous views are taking of both the sides and bottom of mail items and these views are processed to determine whether or not double-feed has occurred. This can be achieved using either two cameras or a single camera with additional optics.

U.S. Pat. No. 5,502,312 discloses an electro-optical system for double document detection wherein an improved calibration is employed. A microcontroller generates a series of increasingly wider pulses, which are transformed into a series of respective increasingly higher ramp pulses to drive a light emitter at gradually increased power until a predetermined value of an output signal of a light detector is achieved. Then the pulse width corresponding to the predetermined value of the output signal is fixed. During feeding of documents, the microcontroller monitors the output signal to determine a double-feed document condition if the output signal exceeds a predetermined value. To detect a "true" double-feed document condition, a software timer counts a prolongation of the alteration of the output signal. Also, in order not to miss a "true" double-feed document condition when the area of overlapping is small, the distance between a front edge of the first overlapped document and a rear edge of the last overlapped document is measured.

U.S. Pat. No. 6,761,352 concerns a system for detecting overlapped flat objects in a sequence of flat objects have at least one of their edges exposed for viewing as they pass along a feed path. The system includes a sensor for generating a signal in response to detecting a flat object in the feed path and a camera responsive to the signal for capturing a digital image of the exposed edges of the detected flat object in the feed path. A vision system is coupled to the camera for receiving the digital image. The vision system analyzes at least a portion of the image to determine a pixel density variation along a direction perpendicular to the edges and uses the pixel density variation to output an indication of the number of edges in the image.

Though the above double feeds detecting systems prove satisfactory enough, they are not always effective as they do not really address in particular the technical problems related to the variable item thickness (flow of mixed flat items), the perfect superimposition of double-feed, the false double-feed or the material diversity of the flat item.

Accordingly, it is desirable to provide an improved double-feeds detecting system which addresses the shortcomings set forth above.

OBJECTS AND DEFINITION OF THE INVENTION

It is therefore an object of the invention to provide an improved system for efficiently detecting on the fly double-feeds conveyed in a mail processing machine, particularly at high speeds.

Another object of the invention consists in proposing such a double-feed detecting system which allows to bulk process flat items such as postcard or mixed mail of variable thickness.

Another object of the invention is to solve the problem of perfectly superimposed flat items.

Another object of the invention is to also solve the problem of false double-feeds originated from special types of flat items incorrectly identified.

According to a first aspect of the invention, these objects are achieved through the provision of a system for detecting on the fly double-feed flat items such as documents or mail articles conveyed in a mail processing machine, comprising:
  at least one detection device mounted on a support element of the mail processing machine at a tilt angle α in relation to a transport deck which is selected so as to scan a front end part and a front face of the moving flat items, for directing a beam of radiant energy from a radiation source toward the moving flat items, scanning them with the beam and receiving at least a portion of the beam of radiation reflected from them, the at least one detection device comprising:
  a triangulation sensor for providing an output proportional to a position at which the reflected portion of the beam is received on it, and means for determining from said output, the distance d between the radiation source and the point of reflection of the beam on the moving flat items, and providing a signal S representative of said distance; and
  a controller configured to receive the signal S from the triangulation sensor and generate an output signal V indicative of both a flat item profile and a double-feed condition when it detects a significant break point or change in slope of the output signal V from a first direction to a second direction.

The analysis and interpretation of the resulting flat item profile prove to be a simple and reliable way for easily differentiating true double feed conditions from false ones without any substantial and time-consuming operator involvement because of correcting and checking actions. Scanning of the front end of the flat item also allows detecting perfect double-feeds during a bulk processing. Even if the double-feed rate rarely exceeds 0.5%, these technical advantages actually matter for customers using intensively mail processing machines.

According to a preferred embodiment, the radiation source comprises a laser.

Laser detection permits solving recurrent issues with paper color or type and continual calibration while automatically providing a precise detailed profile of the flat item.

Preferably, the tilt angle α is selected so as to take into account at least one of the following parameters: flat item thickness, measuring distance range, size of spot, transport speed and flat item kind.

According to another embodiment, the support element comprises means for adjusting the angular position of the at least one detection device in relation to the transport deck and in accordance with the thickness of the flat item. For a predefined measuring distance range, the tilt angle α increases with the thickness of the flat item.

Preferably, the tilt angle α is within the range of 20° to 80° for a flat item thickness up to 20 mm.

Advantageously, the controller is integrated within the at least one detection device, and customized with software applications dedicated to double-feed detection.

According to still another embodiment, two detection devices are coupled with two different tilt angles α1 and α2 for respectively providing a signal S1 assigned to thin flat items and a signal S2 assigned to thick flat items.

According to yet another embodiment, the double-feed detecting system further comprises a thickness estimation device located upstream the two detection devices for classifying thin and thick flat items in accordance with the determined thickness range assigned to each of the two detection devices.

Advantageously, the double-feed detecting system comprises a profile database including typical signal profiles associated with the flat item kind and dimensions for removing any uncertainty during the double feed detection with regards to a flap edge, a seam overlap, an envelope window, a paper crease, fold or bump. Preferably, the length of the flat item is derived from its scanned profile and the transport speed for validating the double-feed detection.

BRIEF DESCRIPTION OF DRAWINGS

The invention can be better understood in reading the following detailed description accompanied by illustrative and non-limiting examples with reference to the drawings, in which.

DETAILED DESCRIPTION OF PREFERRED EMBODIMENT

The present invention provides a system for detecting on the fly double-feed flat items such as documents or mail articles conveyed in a mail processing machine such as a franking, sorting or inserting machine, particularly flat at high throughput or speed.

Figure 1:
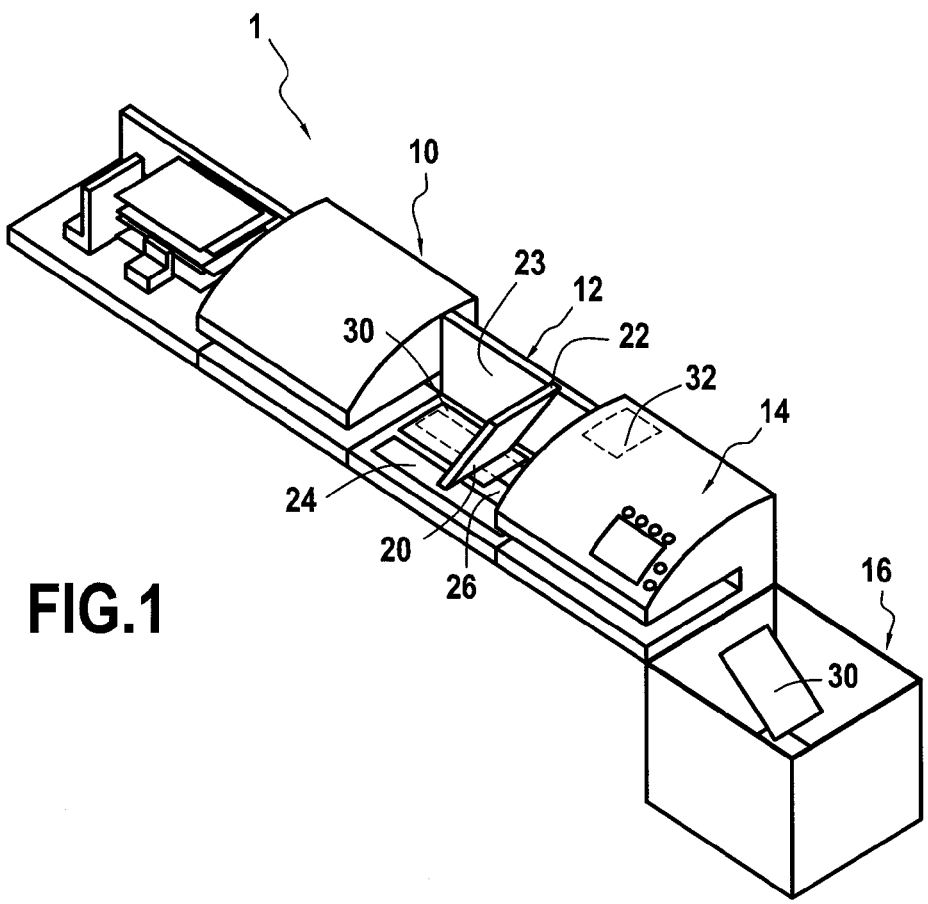
FIG. 1 is a diagrammatic view of a typical mail processing machine in which a double-feed detecting system according to the invention is put into a conveying module.

FIG. 1 shows a mail processing machine 1 comprising, in the direction of movement of the mail items, and without the following list being limiting: a feeding and singulating module 10, a conveying module 12, a franking module 14 and a stacking module 16.

According to the invention, such mail processing machine comprises a laser double-feed detection device 20 which is mounted on a pivoting support element 22 fixed itself to a registering wall 23 of conveying module 12. The laser double-feed detection device is located just above transport belts 24 of the conveying module at a tilt angle α in relation to the transport deck 26 selected so that the laser beam scans both the front end part and the front face of the flat items 30, 30' as explained below in regards to FIGS. 3A and 3B.

Figure 2:
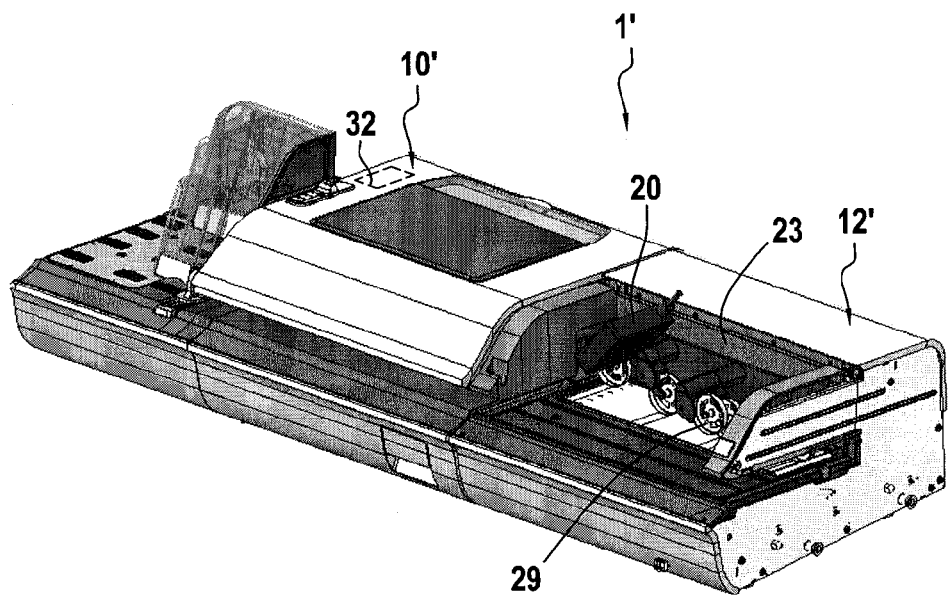
FIG. 2 is a view illustrating in more detail a double-feed detecting system according to the invention installed in a weighing module.

FIG. 2 only illustrates a more detailed integration of laser double-feed detection device 20 within a weighing module 12' located right downstream a feeding module 10' of a postage metering machine 1'. Preferably, the moving flat items are gently pressed against the transport deck, e.g. by pressing brushes or rollers 29 and nudged against the registering wall, e.g. by biased rollers or belts. This arrangement provides by the way a more precise registering and measurement of thickness. A special module assigned to double-feed detection only is also an option.

Conventionally the laser double-feed detection device directs a laser beam from a radiation source toward the moving flat items, scans them with the beam and receives at least a portion of the beam reflected from them. It includes a triangulation sensor 20a, 20a' for providing an output proportional to the position at which the reflected portion of the beam is received on the sensor, and means for determining from said output, the distance between the laser source and a point of reflection of the beam on the moving flat items, and providing a signal S representative of said distance.

Figure 3A:
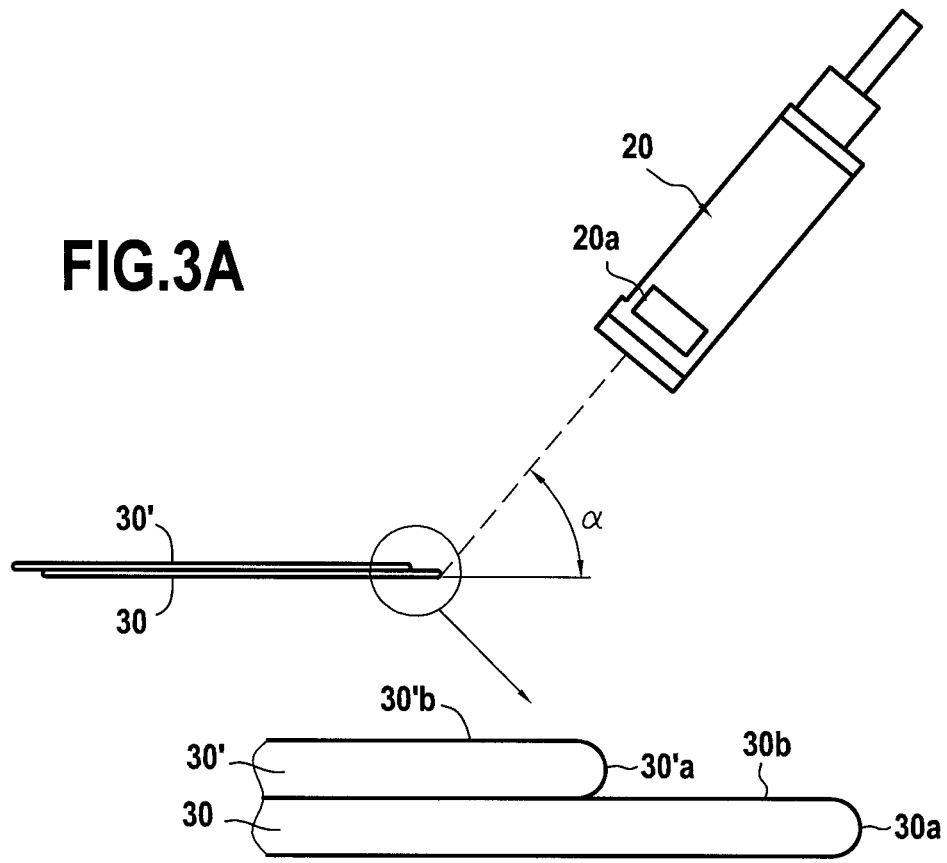
FIG. 3A is a schematic side view of a laser detection device according to the invention for detecting overlapped double-feeds.
Figure 4A:
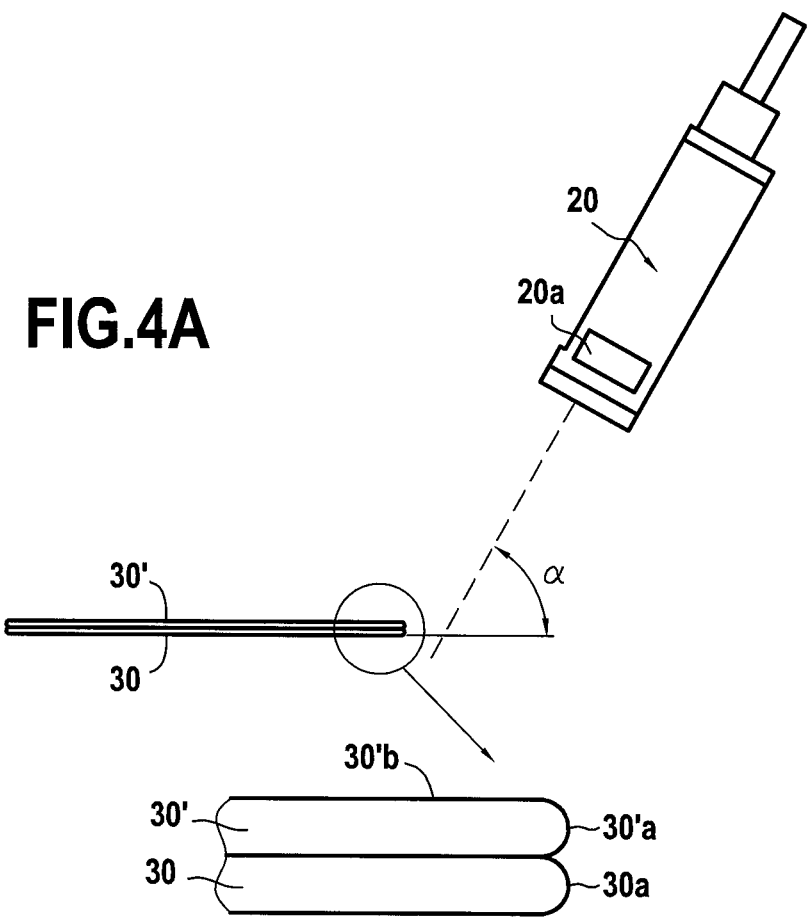
FIG. 4A is a schematic side view of a laser detection device according to the invention for detecting perfect double-feeds.
Figure 5:
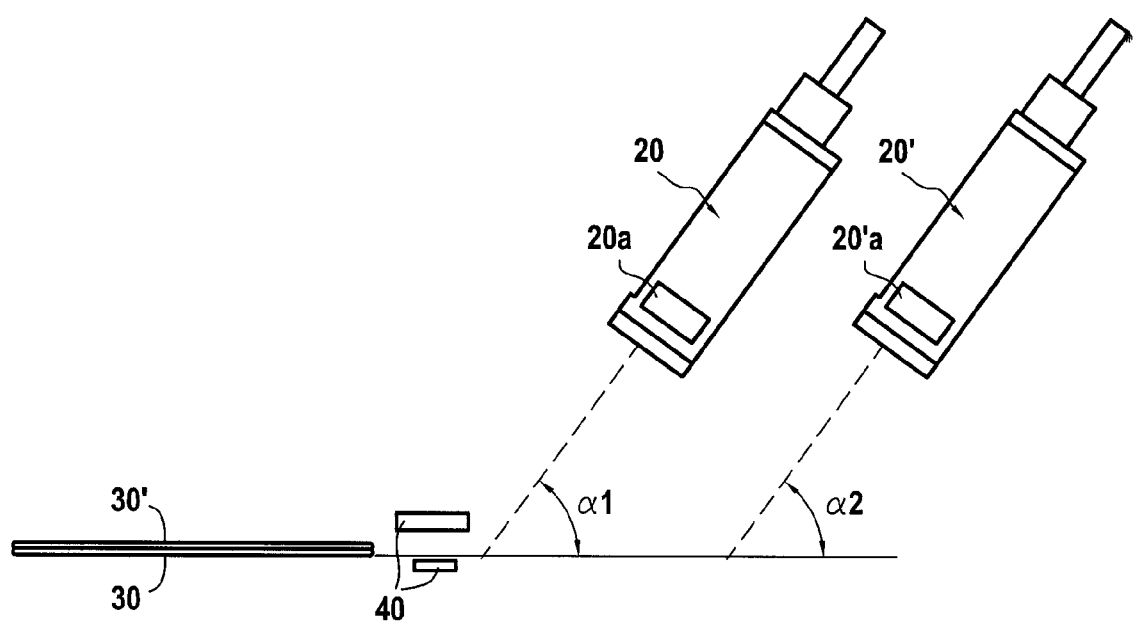
FIG. 5 is a schematic side view of a double-feed detecting system variant for finely detecting double-feeds.

A controller 32 of the mail processing machine is classically configured to receive the signal S from the triangulation sensor and generate an output signal V indicative of a flat item profile. It provides in particular a double-feed condition when it detects a significant break point or change in slope of the signal from a first direction to a second direction. This is rendered possible by the novel arrangement consisting in inclining the laser double-feed detection device so as to scan with the laser beam both the front end part 30a, 30a' and the front face 30b, 30b' of the moving flat item. The tilt angle α as illustrated on FIG. 3A, FIG. 4A and FIG. 5, is selected so as to optimally take into account at least one of the following parameters: flat item thickness, measured distance range, standoff, size of spot, transport speed and flat item kind. It is within the range of 20° to 80° for processing bulk mail with a thickness up to 20 mm and a laser distance range of 20 to 60 mm. For a predefined distance range, a thin envelope requires a small tilt angle that provides advantageously a longer measuring duration between the front edges of double-feed whereas a thick envelope requires a large tilt angle.

| Double-feed thickness | Tilt angle | Measurement duration |
|---|---|---|
| 2 × 0.6 mm | 70° | 0.4 ms |
| | 50° | 0.5 ms |
| 2 × 4.0 mm | 70° | 2.0 ms |
| | 50° | 3.5 ms |

| Measuring distance range | Minimal tilt angle for a double-feed of 20 mm thickness |
|---|---|
| 25 mm | 53° |
| 50 mm | 24° |

On FIG. 1 the support element 22 incorporates means for adjusting the angular position of laser double-feed detection device 20 in relation to the transport deck 26.

Figure 3B:
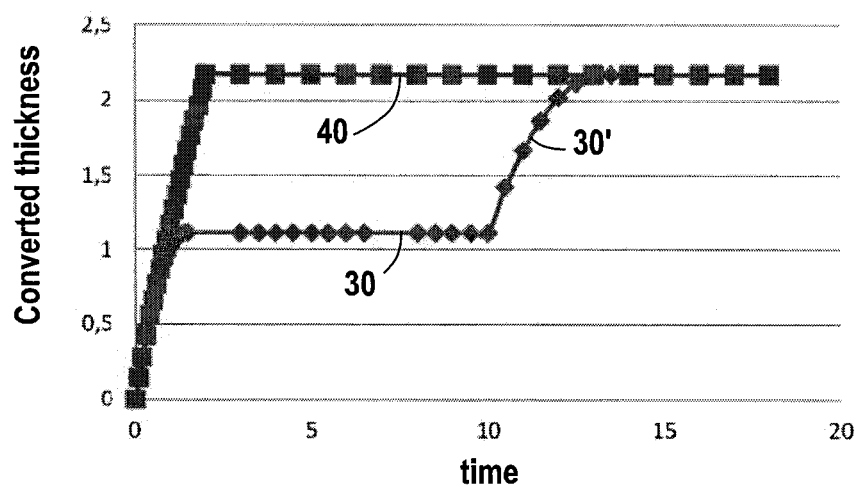
FIG. 3B is graphical plot illustrating the thickness profile comparison according to the invention between a usual double-feed and a single flat item of the same thickness, and corresponding to FIG. 3A.

With reference to FIG. 3A and FIG. 3B, it can be noted that the graphical plot dearly illustrates the thickness profile comparison according to the invention between a usual double feed and a single flat item of the same thickness. The shift between the two envelopes equals 10 mm here, the transport speed 1 m/s, the tilt angle 50° and it took around 10 ms for detecting the double-feed formed by two envelopes 30, 30' of about 1.1 mm thick each. Curve 40 corresponds to the thickness profile of a single envelope of the same cumulated thickness of 2.2 mm.

Figure 4B:
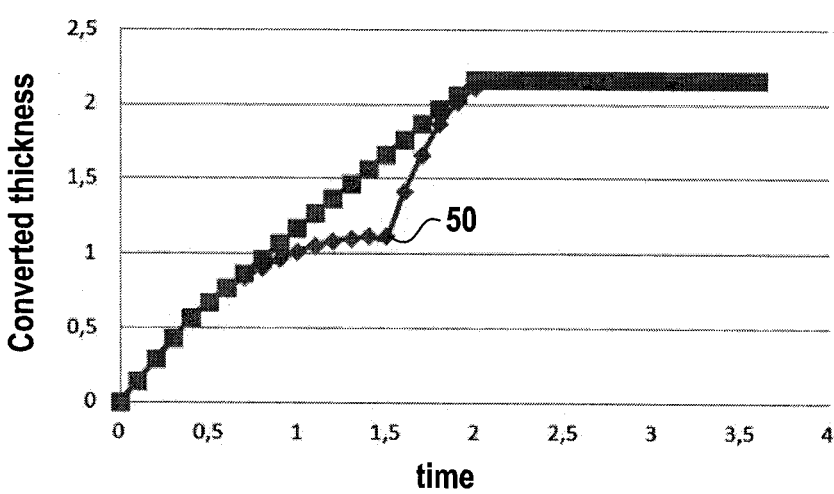
FIG. 4B is a graphical plot illustrating the thickness profile comparison according to the invention between a perfect double-feed and a single flat item of the same thickness, and corresponding to FIG. 4A.

On FIG. 4A and FIG. 4B it took only 1.5 ms for detecting a similar double-feed based this time on two perfectly superimposed envelopes. Scanning of only the aligned front edges of envelopes 30, 30' provides the significant break point 50 where is a strong change of slope from a first direction to a second direction.

Quite importantly, the double-feed detecting system comprises a profile database including typical signal profiles associated with the flat item kind and dimensions that allows removing any uncertainty during the double-feed detection cycle, e.g. with regards to a flap edge, a seam overlap, an envelope window, a paper crease, fold or bump. Preferably, the profile database is incorporated in the controller 32 which is itself advantageously integrated within the laser double-feed detection device, and customized with software applications dedicated to double-feed detection.

FIG. 5 illustrates another embodiment in which two laser double-feed detection devices 20, 20' have two different tilt angles α1 and α2 for respectively providing a signal S1 assigned to thin flat items, e.g. up to 1 mm, and a signal S2 assigned to thick flat items, e.g. from 1 mm to 20 mm. Preferably, for categorizing the moving flat items, a rough thickness value is also provided by a thickness estimation device 40 located upstream the two laser double-feed detection devices.

While this invention has been described with reference to illustrative embodiments, it is not intended to be construed in a limiting sense. Various modifications and combinations of these illustrative embodiments will be apparent to persons skilled in the art upon reference to the description and are specifically contemplated to be within the scope of the invention. For example the length of flat items is determined from their scanned profile and the transport speed for validating the double-feed detection.

The invention claimed is:

1. A system for detecting on the fly double-feed flat items such as documents or mail articles conveyed in a mail processing machine, comprising:
    at least one detection device mounted on a support element of the mail processing machine at a tilt angle α in relation to a transport deck which is selected so as to scan a front end part and a front face of the moving flat items, for directing a beam of radiant energy from a radiation source toward the moving flat items, scanning them with the beam and receiving at least a portion of the beam of radiation reflected from them, the at least one detection device comprising:
        a triangulation sensor for providing an output proportional to a position at which the reflected portion of the beam is received on it, and means for determining from said output, the distance d between the radiation source and the point of reflection of the beam on the moving flat items, and providing a signal S representative of said distance; and
    a controller configured to receive the signal S from the triangulation sensor and generate an output signal V indicative of both a flat item profile and a double-feed condition when it detects a significant break point or change in slope of the output signal V from a first direction to a second direction.

2. The double-feed detecting system of claim 1, wherein the radiation source comprises a laser.

3. The double-feed detecting system of claim 1, wherein the tilt angle α is selected so as to take into account at least one of the following parameters: flat item thickness, measuring distance range, standoff, size of spot, transport speed and flat item kind.

4. The double-feed detecting system of claim 1, wherein the support element comprises means for adjusting the angular position of the at least one detection device in relation to the transport deck and in accordance with the thickness of the flat item.

5. The double-feed detecting system of claim 4, wherein, for a predefined measuring distance range, the tilt angle α increases with the thickness of the flat item.

6. The double-feed detecting system of claim 4, wherein the tilt angle α is within the range of 20° to 80° for a flat item thickness up to 20 mm.

7. The double-feed detecting system of claim 1, wherein the controller is integrated within the at least one detection device, and customized with software applications dedicated to double-feed detection.

8. The double-feed detecting system of claim 1, wherein two detection devices are coupled with two different tilt angles α1 and α2 for respectively providing a signal S1 assigned to thin flat items and a signal S2 assigned to thick flat items.

9. The double-feed detecting system of claim 8, wherein it further comprises a thickness estimation device located upstream the two detection devices for classifying thin and thick flat items in accordance with the determined thickness range assigned to each of the two detection devices.

10. The double-feed detecting system of claim 1, wherein the length of the flat item is derived from its scanned profile and the transport speed for validating the double-feed detection.

11. The double-feed detecting system of claim 1, wherein it further comprises a profile database including typical signal profiles associated with the flat item kind and dimensions for removing any uncertainty during the double feed detection with regards to a flap edge, a seam overlap, an envelope window, a paper crease, fold or bump.

12. The double-feed detecting system of claim 1, wherein the moving flat items are pressed against the transport deck by pressing brushes or rollers, and nudged against a registering wall by biased rollers or belts.

13. The double-feed detecting system of claim 1, wherein the at least one detection device is integrated in a conveying or weighing module of a mail processing machine such as a franking, sorting or inserting machine.

* * * * *